(12) United States Patent
Gagliardi et al.

(10) Patent No.: US 9,242,788 B2
(45) Date of Patent: Jan. 26, 2016

(54) PACKAGE OF ABSORBENT ARTICLES

(71) Applicant: The Procter & Gamble Company, Cincinnati, OH (US)

(72) Inventors: Ivano Gagliardi, Pescara (IT); Florian Phillip Rousselange, Neu-isenburg (DE); Uwe Jürgen Van De Loo, Stimpfach (DE)

(73) Assignee: The Procter & Gamble Company, Cincinnati, OH (US)

( * ) Notice: Subject to any disclaimer, the term of this patent is extended or adjusted under 35 U.S.C. 154(b) by 97 days.

(21) Appl. No.: 14/135,774

(22) Filed: Dec. 20, 2013

(65) Prior Publication Data

US 2015/0175345 A1 Jun. 25, 2015

(51) Int. Cl.
| | |
|---|---|
| *A61B 17/06* | (2006.01) |
| *B65D 85/16* | (2006.01) |
| *B65D 85/62* | (2006.01) |
| *A61F 13/15* | (2006.01) |
| *A61F 13/47* | (2006.01) |
| *A61F 13/551* | (2006.01) |
| *B65B 11/06* | (2006.01) |
| *B65D 71/06* | (2006.01) |
| *A61F 13/472* | (2006.01) |

(52) U.S. Cl.
CPC .......... *B65D 85/62* (2013.01); *A61F 13/15723* (2013.01); *A61F 13/47* (2013.01); *A61F 13/47254* (2013.01); *A61F 13/55145* (2013.01); *B65B 11/06* (2013.01); *B65D 71/06* (2013.01); *A61F 2013/4708* (2013.01); *B65D 2571/00901* (2013.01)

(58) Field of Classification Search
CPC .... B65D 69/00; B65D 83/0835; B65D 85/16; B65D 2203/00; A61F 15/001
USPC ................. 206/494, 499, 526, 570, 440, 449; 604/385.04, 387
See application file for complete search history.

(56) References Cited

U.S. PATENT DOCUMENTS

| | | | |
|---|---|---|---|
| 4,394,898 A | 7/1983 | Campbell | |
| 4,912,992 A | 4/1990 | Kinoshita et al. | |
| 5,827,251 A | 10/1998 | Moder et al. | |
| 5,934,470 A | 8/1999 | Bauer et al. | |
| 5,971,153 A | 10/1999 | Bauer et al. | |
| 6,761,013 B2 | 7/2004 | Tippey et al. | |
| D496,273 S | 9/2004 | Lenz et al. | |
| 6,923,321 B2 * | 8/2005 | Samolinski et al. | 206/440 |
| 7,000,764 B2 * | 2/2006 | Otsubo | 206/494 |
| 7,028,841 B2 | 4/2006 | Otsubo | |
| 7,048,124 B2 | 5/2006 | Osterdahl et al. | |
| 7,059,474 B2 | 6/2006 | Tippey | |

(Continued)

FOREIGN PATENT DOCUMENTS

| | | |
|---|---|---|
| EP | 1140662 A1 | 10/2001 |
| GB | 2269162 A | 2/1994 |
| WO | WO93/15700 A1 | 8/1993 |

OTHER PUBLICATIONS

PCT International Search Report, mailed Feb. 27, 2015, 107 pages.

*Primary Examiner* — Chun Cheung
(74) *Attorney, Agent, or Firm* — Andrew J. Hagerty

(57) ABSTRACT

Packages are described that balance the need for efficient packing of a plurality of absorbent articles within the package and a consumer's ability to easily discern and remove individual articles.

14 Claims, 3 Drawing Sheets

(56) References Cited

U.S. PATENT DOCUMENTS

| | | |
|---|---|---|
| 7,150,137 B2 | 12/2006 | Tippey et al. |
| 7,353,949 B2 | 4/2008 | Osterdahl et al. |
| 8,261,914 B2 * | 9/2012 | Hooyman et al. ............ 206/494 |
| 2004/0195137 A1 * | 10/2004 | Otsubo ........................ 206/494 |
| 2005/0222550 A1 | 10/2005 | Mitsui et al. |
| 2005/0288643 A1 | 12/2005 | Mizutani et al. |
| 2006/0074390 A1 * | 4/2006 | Price et al. .................... 604/357 |
| 2007/0233031 A1 | 10/2007 | Benson et al. |

* cited by examiner

PACKAGE OF ABSORBENT ARTICLES

FIELD OF THE INVENTION

The present invention is directed to packages of absorbent articles, and methods for making and packaging a plurality of absorbent articles. The absorbent articles are generally designed and configured to manage bodily exudates such as urine, menses, or other vaginal discharges. Exemplary absorbent articles include diapers, sanitary napkins, pantiliners, and adult incontinence pads and liners.

BACKGROUND OF THE INVENTION

Flexible polymeric bags and cardboard cartons are two common forms of absorbent article packages commercially available today. For a variety of reasons, including costs and disposal waste volume, the packages can be tightly/efficiently packed with the absorbent articles. This can make removing individual absorbent articles challenging, particularly when the package is on the fuller side and/or when the articles are very thin (e.g., overall caliper of 1 to 5 millimeters). The present invention provides one or more solutions that balance the need for efficiently packed packages and a consumer's ability to easily remove individual articles from the same.

SUMMARY OF THE INVENTION

The present invention is directed to packages of absorbent articles. In accordance with one exemplary embodiment, there has now been provided a package comprising a container comprising an interior volume, a first absorbent article disposed within the interior volume, and a second absorbent article disposed within the interior volume. Each of the first absorbent article and the second absorbent article comprises a longitudinal axis and a transverse axis. The first and second absorbent articles are positioned within the interior volume so that the longitudinal axis of the first absorbent article is not parallel to the longitudinal axis of the second absorbent article.

In accordance with a second exemplary embodiment, there has now been provided a package comprising the package comprising a container comprising an interior volume, a first absorbent article disposed within the interior volume, and a second absorbent article disposed adjacent the first absorbent article and within the interior volume. Each of the first absorbent article and the second absorbent article comprises a first end having a maximum transverse dimension that is greater than that of a second. The first and second absorbent articles are in an un-folded state within the interior volume. And the first end of the first absorbent article is proximate to the second end of the second absorbent article within the interior volume.

In accordance with a third exemplary embodiment, there has now been provided a package comprising a container comprising an interior volume, a first absorbent article disposed within the interior volume in a first orientation, and a second absorbent article disposed within the interior volume in a second orientation that is different from the first orientation. The first and second absorbent articles are in an un-folded state within the interior volume.

The present invention is also directed to methods for making and packaging a plurality of absorbent articles. In accordance with one exemplary embodiment, there has now been provided a method comprising the steps of delivering a layer of absorbent material in a machine direction; cutting the layer of absorbent material in a cross direction to define a plurality of absorbent cores wherein more than a single absorbent core exists along a line in the cross direction; arranging the plurality of absorbent cores so that there is only a single absorbent core in the cross direction; combining the absorbent cores with a topsheet and a backsheet to define a plurality of absorbent articles each of which comprising an article first end having a maximum transverse dimension that is greater than that of an article second end; and placing the plurality of absorbent articles within a container wherein the article first end of one of the plurality of absorbent articles is proximate to the article second end of an adjacent one of the plurality of absorbent articles.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein.

DETAILED DESCRIPTION OF THE INVENTION

The following text sets forth a broad description of numerous different embodiments of the present invention. The description is to be construed as exemplary only and does not describe every possible embodiment since describing every possible embodiment would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
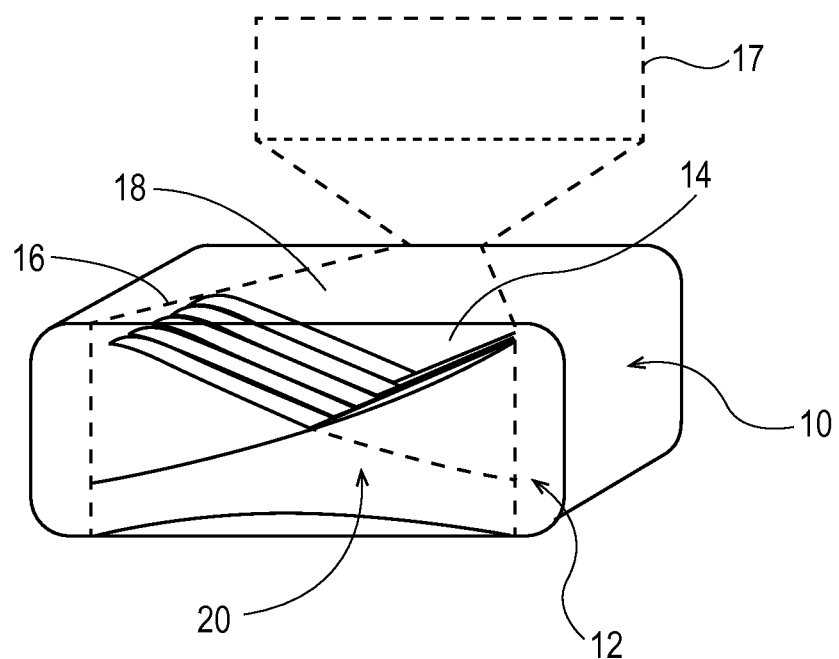
FIG. 1 is a perspective view of an exemplary package embodiment of the present invention.

The present invention is directed to packages of absorbent articles. An exemplary package 10 is shown in FIG. 1. Exemplary package 10 comprises a sheet of material 12 configured to define an interior volume 14 that contains a plurality of absorbent articles 20. A line of weakness 16 is imparted to the sheet of material 12 to enable a flap 17 to be at least partially separated from the remainder of the package to create an opening 18 to allow access to absorbent articles 20. Broken lines are employed in FIG. 1 to show flap 17 in an open position.

Packages of the present invention can be made from a variety of materials, including, for example, cardstock, foils, polymeric films, woven fabrics, nonwovens, and combinations thereof. Sheets of these materials can comprise one layer or multiple layers of similar or dissimilar makeup. Exemplary packages include cardboard cartons and bags constructed from polyolefin-based film stocks (for example, polypropylene or polyethylene). The size, configuration, and opening mechanisms can vary to that shown in FIG. 1.

Figure 2:
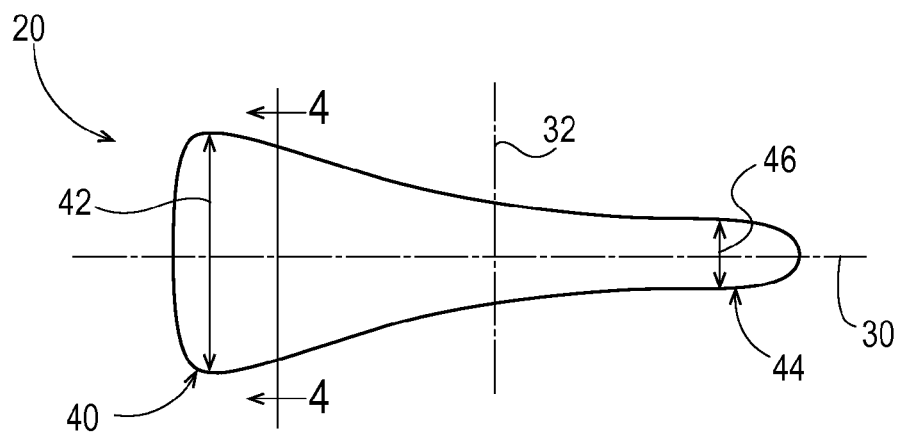
FIG. 2 is a plan view of an exemplary absorbent article that can be included within packages of the present invention.

FIG. 2 shows an individual one of the plurality of absorbent articles 20. Exemplary article 20 has a longitudinal axis 30 and a transverse axis 32 situated orthogonal thereto. Article 20 has a first end 40 that has a maximum transverse dimension 42, and a second end 44 that has smaller maximum transverse dimension 46 than that of first end 40. The transverse dimension difference between first end 40 and second end 44 is large in exemplary article 20. This design is suitable for use in thong-style undergarments. Other asymmetric configurations are contemplated by the present invention, including those where the differences in transverse (or longitudinal) dimension are less than that shown in FIG. 2. It should be appreciated that the packages of the present invention are not limited to containing asymmetric articles such as those shown in the figures.

Figure 3:
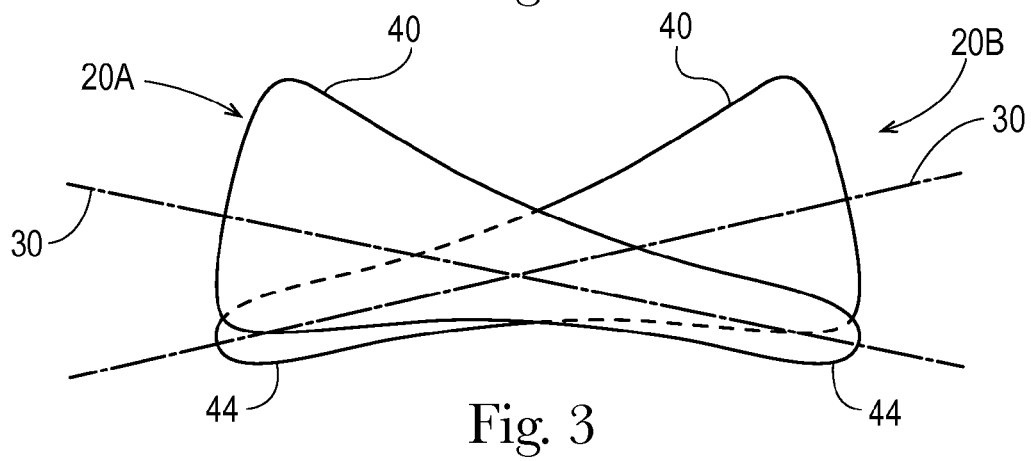
FIG. 3 shows first and second absorbent articles as they are positioned within some package embodiments of the present invention.

FIG. 3 illustrates the first and second absorbent articles 20A, 20B as they are positioned within package 10 in FIG. 1, each having different orientation aspects with respect to the other. Note that the first end 40 of first absorbent article 20A faces the second end 44 of second absorbent article 20B while the second end 44 of first absorbent article 20A faces the first end 40 of second absorbent article 20B. The longitudinal axis 30 of the first absorbent article 20A is also not parallel to the longitudinal axis 30 of the second absorbent article 20B. The orientation aspects shown in FIG. 3 are illustrative only; other orientation aspects are contemplated by the present invention. As can be envisioned from FIG. 1, consumers can discern and more easily retrieve individual absorbent articles from packages of the present invention when the articles are oriented different from those around them when in the interior volume of the packages.

The absorbent articles 20 in package 10 are shown FIG. 1 in an un-folded state and without an optional individual wrapper feature. In alternative embodiments of the present invention, the absorbent articles can be folded (e.g., bi-folded or tri-folded) and/or packaged in individual wrappers. Such secondary packaging is known to the skilled artisan, and can be made out of flexible polymeric films or nonwovens. These individual wrappers can take on a variety of configurations, such as a pouch that can facilitate disposal of a soiled absorbent article.

Figure 4:
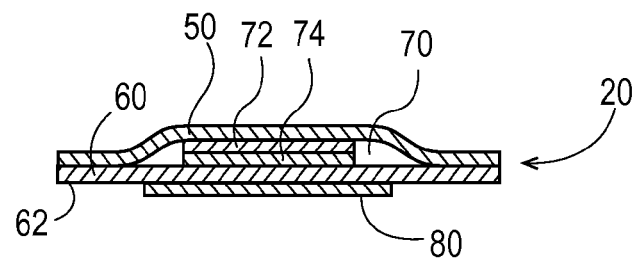
FIG. 4 is a cross-sectional view of the absorbent article in FIG. 2 taken along line IV-IV.

A cross-section of exemplary absorbent article 20 is shown in FIG. 4 as taken through line IV-IV in FIG. 2. Article 20 is shown having a topsheet 50, an opposing backsheet 60, and an absorbent core 70 disposed therebetween. Absorbent core 70 is shown as having two layers 72 and 74; however, a single layer or more than two layers can optionally be employed. In some embodiments, the absorbent articles are very thin articles; for example, 0.5-5 millimeters, 1-4 millimeters, or 1.5-3.5 millimeters in overall caliper. Absorbent articles that are intended to be worn in one's undergarments can employ fastening means for temporarily affixing the article to the undergarment. A layer of adhesive 80 is shown on an outer surface 62 of the backsheet 60. The shape of the adhesive area may also be different than that show; for example, it is also common to use one or two or more strips of longitudinally oriented adhesive strips instead of full coverage. The adhesive strips may then be continuous or intermittent. For example, two longitudinally oriented strips, one on each side of the longitudinal axis, may be applied. The adhesive may be applied via direct slot coating application process. Mechanical adhesive means may be also provided, such as microscopic hooks placed on the backsheet and designed to attach to the fibers present in some undergarments, as in a hook-and-loop fastener.

While the present invention is not limited to packages of absorbent articles having the components and configuration as shown in FIG. 4, these particular components will now be discussed. The topsheet is typically the layer of the absorbent article that is oriented towards and contacts the body of the wearer, and is therefore the first layer to receive bodily exudates. The topsheet is normally made of a single layer, but may also comprise more than one layer (for example a central topsheet layer and two overlapping lateral stripes, as disclosed in WO93/09744 or EP766,953). The topsheet is normally liquid pervious. The term "liquid pervious" as used herein refers to components that allow liquids to pass therethrough without significantly retarding or obstructing the transmission of such liquids therethrough.

It is envisaged that any conventional topsheet materials may be used within the invention. Suitable topsheets may be made for example from nonwoven materials or perforated polyolefinic films. An exemplary topsheet suitable for use herein is a relatively hydrophobic 20 gsm spunbonded nonwoven web comprising bicomponent fibers of the sheath core type (PP/PE).

If desired, the topsheet may be treated with a surfactant to enhance liquid penetration to an underlying absorbent core. The surfactant is typically non-ionic and should be nonirritating to the skin. A surfactant density of about 0.01 milligrams per square centimeter of topsheet area is normally suitable. An exemplary surfactant is sold by the Glyco Chemical, Inc. of Greenwich, Conn. as Pegosperse 200 ML. The topsheet may have a plurality of apertures or other structures to permit liquids deposited thereon to pass through to the absorbent core more quickly.

The general function of the backsheet is to prevent discharges absorbed by the core from escaping the absorbent article and soiling the wearer or their clothing. The backsheet may be made of any suitable material in particular any standard backsheet materials. These materials are generally flexible, liquid resistant, and liquid impervious. Exemplary backsheet materials include, but are not limited to, polyolefinic films or nonwoven webs. Nonwoven webs may be advantageous because they normally provide better breathability for the articles and may be cheaper than polyolefinic films. For example, a relatively hydrophobic 18 grams per square meter (gsm) spunbonded nonwoven web of 2 denier polypropylene fibers. The backsheet may also be a laminate as is know in the art.

The topsheet and the backsheet can be peripherally joined using known techniques such as heat embossing and ultrasonic bonding. The layers may also be glued to each other. The topsheet may be contiguous with the backsheet with these two layers forming the outer periphery of the article.

The absorbent articles contemplated by the present invention further comprise an absorbent core disposed between the topsheet and the backsheet. As used herein, the term "absorbent core" refers to a material or combination of materials suitable for absorbing, distributing, and storing fluids such as urine, blood, menses, and/or other body exudates. The absorbent core may or may not be affixed to the topsheet and backsheet.

The absorbent core can be made of any suitable materials. Nonlimiting examples of suitable liquid-absorbent materials include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including co-form; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof. The absorbent core can comprise superabsorbent polymer (SAP), normally distributed within a matrix of cellulosic fibers, for example in order to reduce the thickness of the absorbent core.

The absorbent core can be unitary, or can be a laminate of two or more layers. For example, the core can comprise a fluid impermeable barrier layer (e.g. a PE Patch) on its backsheet-facing side to prevent fluids retained by the absorbent core from striking through the pantiliner and soiling adjacent garments. An exemplary PE patch is a 25 gsm poly film available from Britton Taco (UK) under trade name ST-012A-White. Further general information regarding absorbent cores can be found in prior patent publications, see for example PCT publications WO0207662A1 and W09119471.

Figure 5:
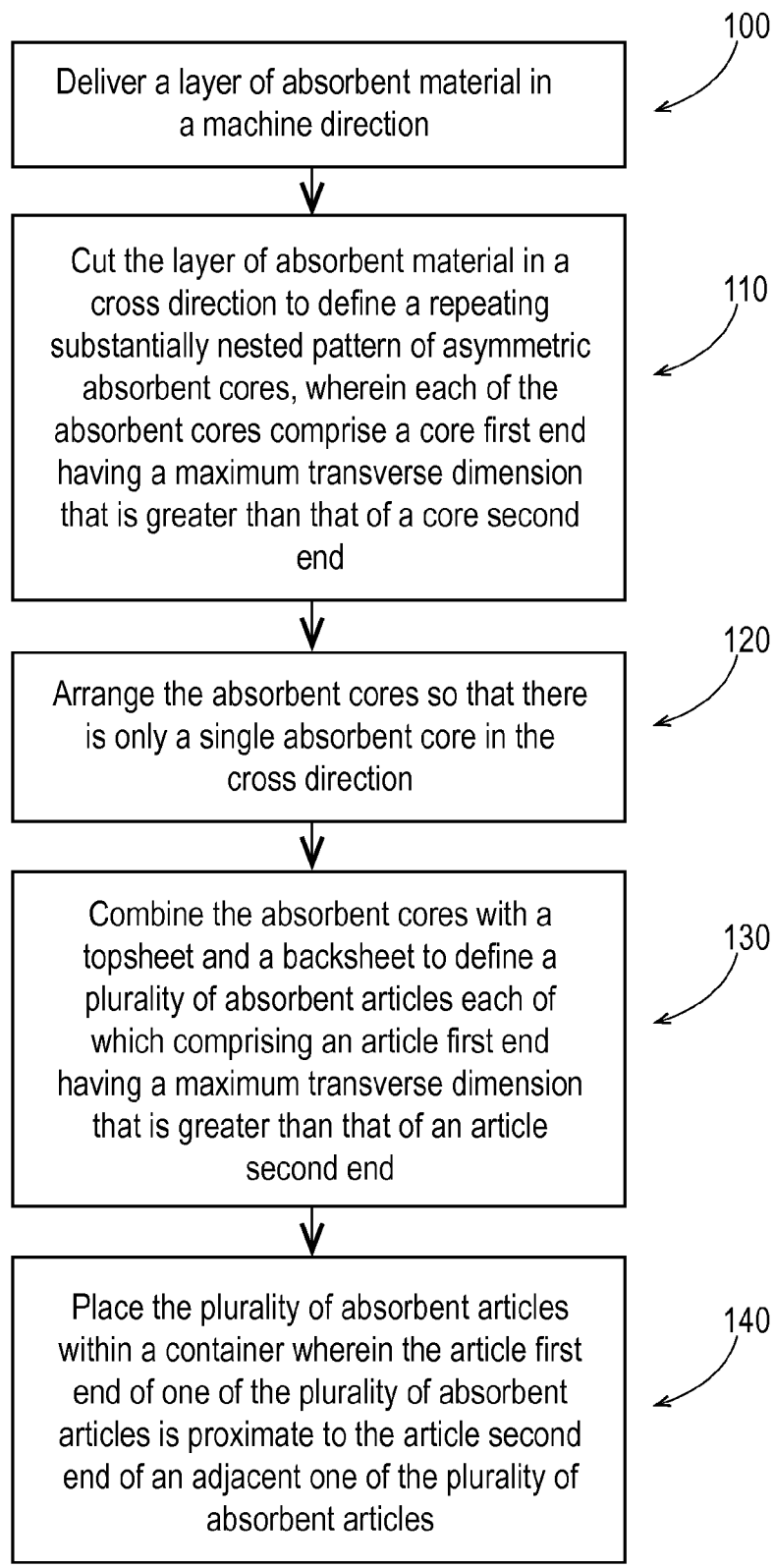
FIG. 5 is a flow chart of an exemplary method embodiment of the present invention.

The present invention is also directed to methods for making and packaging a plurality of absorbent articles. FIG. 5 shows one exemplary method via a flow chart. Step 100 comprises delivering a layer of absorbent material in a machine direction. Step 110 comprises cutting the layer of absorbent material in a cross direction to define a plurality of absorbent cores wherein more than a single absorbent core exists along a line in the cross direction. Step 120 comprises arranging the plurality of absorbent cores so that there is only a single absorbent core in the cross direction. Step 130 comprises combining the absorbent cores with a topsheet and a backsheet to define a plurality of absorbent articles each of which comprising an article first end having a maximum transverse dimension that is greater than that of an article second end. And step 140 comprises placing the plurality of absorbent articles within a container wherein the article first end of one of the plurality of absorbent articles is proximate to the article second end of an adjacent one of the plurality of absorbent articles. In some embodiments, step 110 results in the plurality of absorbent cores being arranged in a substantially nested pattern of asymmetric absorbent cores, wherein each of the absorbent cores comprise a core first end having a maximum transverse dimension that is greater than that of a core second end.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package of absorbent articles, the package comprising:
   a. a container comprising an interior volume;
   b. a first absorbent article disposed within the interior volume, the first absorbent article comprising a first topsheet layer that is liquid permeable and defines the body contacting surface, a first backsheet layer that is liquid impermeable; and
   c. a second absorbent article disposed within the interior volume;
   d. wherein each of the first absorbent article and the second absorbent article comprises a longitudinal axis and a transverse axis;
   e. wherein the first and second absorbent articles are positioned within the interior volume so that the longitudinal axis of the first absorbent article is not parallel to the longitudinal axis of the second absorbent article; and
   f. wherein the first topsheet layer is positioned at the interface between the first absorbent article and the second absorbent article.

2. The package of claim 1, wherein the first and second absorbent articles are in an un-folded state when disposed within the interior volume.

3. The package of claim 1, wherein the first and second absorbent articles are not wrapped in individual wrappers.

4. The package of claim 1, wherein the first and second absorbent articles are asymmetric shaped articles.

5. The package of claim 1, wherein each of the first absorbent article and the second absorbent article comprises an absorbent core that is asymmetric.

6. The package of claim 1, wherein each of the first absorbent article and the second absorbent articles is a pantiliner.

7. A package of absorbent articles, the package comprising:
   a. a container comprising an interior volume;
   b. a first absorbent article disposed within the interior volume, the first absorbent article comprising a first topsheet layer that is liquid permeable and defines the body contacting surface, a first backsheet layer that is liquid impermeable; and
   c. a second absorbent article disposed adjacent the first absorbent article and within the interior volume;
   d. wherein the first and second absorbent articles are in an un-folded state within the interior volume;

e. wherein each of the first absorbent article and the second absorbent article comprises a first end having a maximum transverse dimension that is greater than that of a second end;
f. wherein the first end of the first absorbent article is proximate to the second end of the second absorbent article; and
g. wherein the first topsheet layer is positioned at the interface between the first absorbent article and the second absorbent article.

8. The package of claim 7, wherein the first and second absorbent articles are not wrapped in individual wrappers.

9. The package of claim 7, wherein the first and second absorbent articles are asymmetric shaped articles.

10. The package of claim 7, wherein each of the first absorbent article and the second absorbent article is a pantiliner.

11. A package of absorbent articles, the package comprising:
a. a container comprising an interior volume;
b. a first absorbent article disposed within the interior volume in a first orientation, the first absorbent article comprising a first topsheet layer that is liquid permeable and defines the body contacting surface, a first backsheet layer that is liquid impermeable; and
c. a second absorbent article disposed within the interior volume in a second orientation that is different from the first orientation;
d. wherein the first and second absorbent articles are in an un-folded state within the interior volume; and
e. wherein the first topsheet layer is positioned at the interface between the first absorbent article and the second absorbent article.

12. The package of claim 11, wherein the first and second absorbent articles are not wrapped in individual wrappers.

13. The package of claim 11, wherein the first and second absorbent articles are asymmetric shaped articles.

14. The package of claim 11, wherein each of the first absorbent article and the second absorbent article comprises an absorbent core that is asymmetric.

* * * * *